(12) United States Patent
Buchanan et al.

(10) Patent No.: US 6,263,745 B1
(45) Date of Patent: Jul. 24, 2001

(54) FLOW CYTOMETER NOZZLE AND FLOW CYTOMETER SAMPLE HANDLING METHODS

(75) Inventors: Kris S. Buchanan; Lisa A. Herickhoff, both of Fort Collins, CO (US)

(73) Assignee: XY, Inc., Fort Collins, CO (US)

( * ) Notice: Subject to any disclaimer, the term of this patent is extended or adjusted under 35 U.S.C. 154(b) by 0 days.

(21) Appl. No.: 09/454,488

(22) Filed: Dec. 3, 1999

(51) Int. Cl.[7] .................................................. G01N 15/14

(52) U.S. Cl. ............................................................ 73/865.5

(58) Field of Search ........................ 73/865.5; 324/71.4; 356/440–442

(56) References Cited

U.S. PATENT DOCUMENTS

| | | | |
|---|---|---|---|
| 4,362,246 | 12/1982 | Adair | 209/3.3 |
| 4,660,971 | 4/1987 | Sage et al. | 356/39 |
| 4,988,619 | 1/1991 | Pinkel | 435/30 |
| 5,135,759 | 8/1992 | Johnson | 424/561 |
| 5,371,585 | 12/1994 | Morgan et al. | 356/246 |
| 5,439,362 | 8/1995 | Spaulding | 424/185.1 |
| 5,466,572 | 11/1995 | Sasaki et al. | 435/2 |
| 5,483,469 | 1/1996 | Van den Engh et al. | 364/555 |
| 5,602,039 | 2/1997 | Van den Engh | 436/164 |
| 5,602,349 | 2/1997 | Van den Engh | 73/864.85 |
| 5,660,997 | 8/1997 | Spaulding | 435/7.21 |
| 5,690,895 | 11/1997 | Matsumoto et al. | 422/73 |
| 5,700,692 | 12/1997 | Sweet | 436/50 |
| 5,726,364 | 3/1998 | Van den Engh | 73/864.85 |
| 5,985,216 | 11/1999 | Rens et al. | 422/73 |

FOREIGN PATENT DOCUMENTS

| | | |
|---|---|---|
| WO 96/12171 | 4/1996 | (WO) . |
| WO 99/05504 | 7/1998 | (WO) . |
| WO 99/05504 | 2/1999 | (WO) . |

OTHER PUBLICATIONS

Dean, P. N., Pinkel D. and Mendelsob. n, M. L. 1978. Hydrodynamic orientation of spermatozoa heads for flow cytometry. Biophys. J. 23:7–13.

Fulwyler, M. J. 1977. Hydrodynamic orientation of cells. J Histochem. Cytochem. 25:781–783.

Seidel, G. E. Jr., Herickhoff, L. A., Schenk, J.L., Doyle, S.P. and Green, R.D. 1998. Artifical insemination of heifers with cooled, unfrozen, sexed semen. 1998. Theriogenology. 49(1):365.

Johnson, L.A., Welch, G.R., Rens, W. and Dobrinsky, J. R. 1998. Enhanced flow cytometric sorting of manunalian X and Ysperm: high speed sorting and orienting no77.1e for artificial insemination. Theriogenology. 46(1):361. abstr.

(List continued on next page.)

*Primary Examiner*—Robert Raevis
(74) *Attorney, Agent, or Firm*—Santangelo Law Offices, P.C.

(57) ABSTRACT

An improved nozzle system for a flow cytometer and accompanying methods have been invented for a high efficiency orientation and sorting process of a flat sample and dedicates items such as equine or bovine sperm cells. This improved nozzle system comprises a nozzle with a novel interior surface geometry that can both gently accelerate the cells and can include an elliptical-like, single torsional interior surface element within the nozzle, i.e., a single torsional orientation nozzle. The elliptical-like, single torsional interior surface element may have a laminar flow surface and may produce the simplest flow path for applying minimal forces which act in either an accelerative nature or orienting hydrodynamic forces, namely, the single torsional orientation forces, to orient a flat sample such as animal sperm cells into a proper direction for an analyzing and efficiently sorting process in clinical use, for research and for the animal insemination industry.

69 Claims, 6 Drawing Sheets

OTHER PUBLICATIONS

Kachel, V., et al., "Uniform Lateral Orientation, Cused by Flow Forces, of Flat Particles in Flow–Through System", The Journal of Histochemistry and Cytochemistry, 1997, vol. 25, No. 7, pp 774–780.

Rens, W., et al., "A Novel Nozzle for More Efficient Sperm Orientation to Improve Sorting Efficiency of X– and Y–Chromosome–Bearing Sperm", Technical Notes, Cytometry 33, 1998, pp 476–481.

Gurnsey, M. P., and Johnson, L. A., "Recent improvements in efficiency of flow cytometric sorting of X and Y– chromosome bering sperm of domestic animals: a review", 1998, New Zealand Society of Animal Protection, three pages.

Rens, W., et al., "Improved Flow Cytometric Sorting of X—and Y—Chromosome Bearing Sperm: Substantial Increase in Yield of Sexed Semen", Molecular Reproduction and Development, 1999, pp 50–56.

Johnson, L.A., Welch, G. R., Garner DL. 1994. Improved flow sorting resolution of X– and Y– chromosome bering viable sperm separation using dual staining and dead cell gating. Cytometry 17 (suppl 7):83.

Welch G. R., Houck D.W., Johnson L.A., 1994. Fluidic and optical modifications to a FACS IV for flow sorting of X– and Y– chromosome bearing sperm based on DNA. Cytometry 17 (suppl 7): 74.

Johnson L.A., Pinkel D. 1986. Modification of a laser–based flow cytometer for high resolution DNA analysis of mammalian spermatozoa. Cytometry 7:266–273.

Johnson L.A., Flook J.P., Look M.V. 1987. Flow cytometry of X– and Y– chromosome bearing sperm for DNA using an improved preparation method and staining with Hoechst 333–42. Garnete Research 17:203–212.

Johnson L. A., Flook J.P., Hawk H.W. Sex preseletion in rabbits: Live births from X and Y sperm seperated by DNA and cell sorting. Bio Reprod 41: 199–203, 1989.

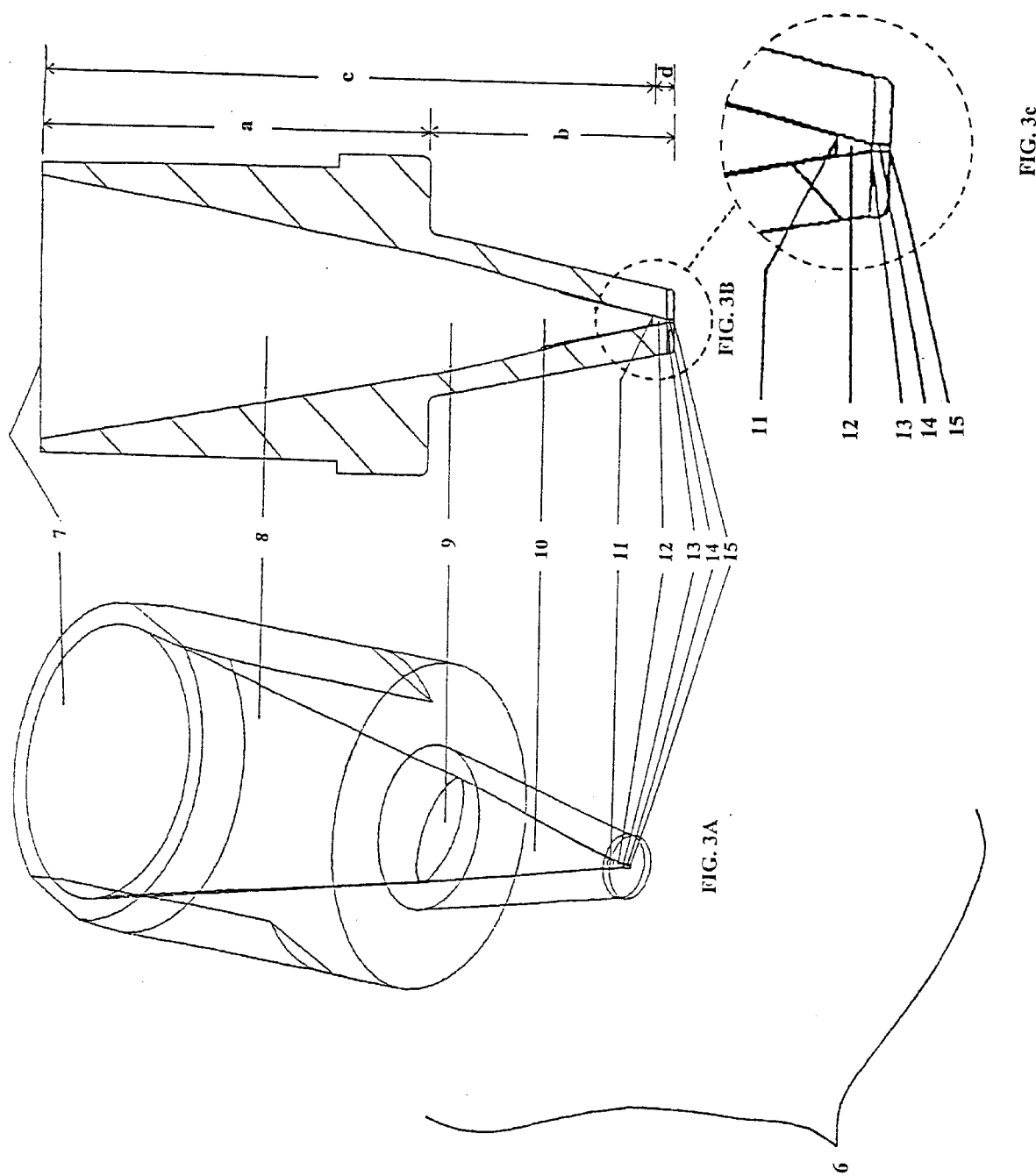

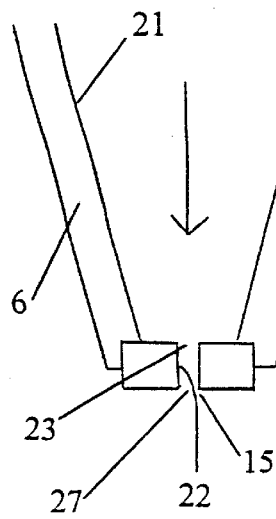
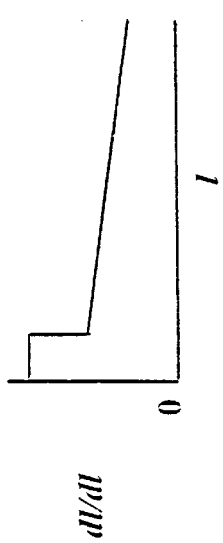
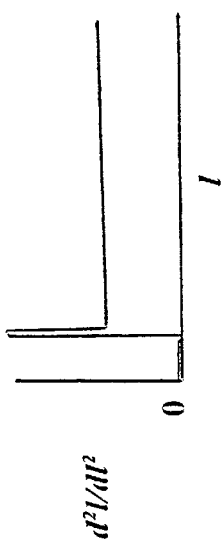
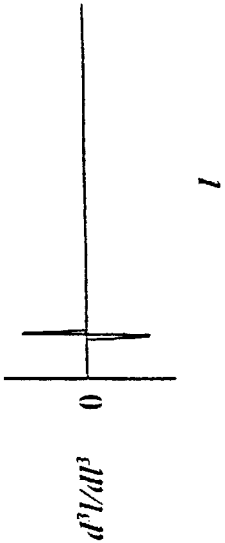
Fig. 6　　　　Fig. 7a　　　　Fig. 7b　　　　Fig. 7c
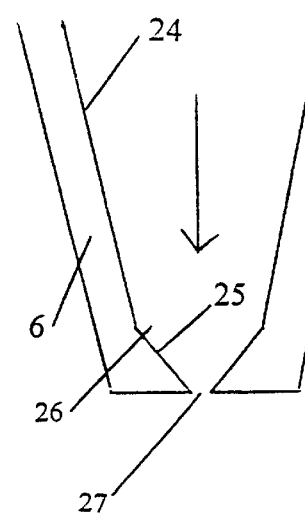
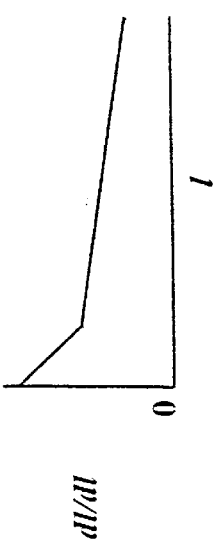
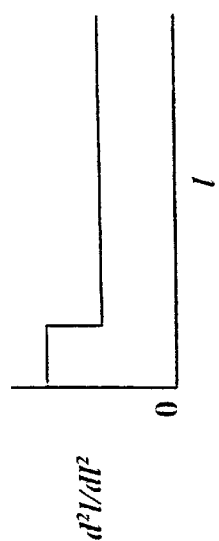
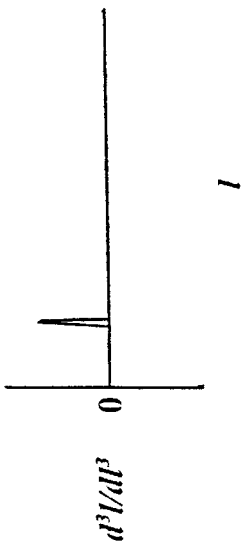
Fig. 8　　　　Fig. 9a　　　　Fig. 9b　　　　Fig. 9c

FLOW CYTOMETER NOZZLE AND FLOW CYTOMETER SAMPLE HANDLING METHODS

This invention relates to an improved nozzle apparatus for a flow cytometer system and methods for improving flow cytometry. Specifically, this invention relates to a novel design of a nozzle interior surface geometry that gently handles and orients a sample into a proper radial direction for analyzing and efficient sorting. The invention also focuses on systems for sorting delicate cells, especially living sperm cells.

BACKGROUND OF THE INVENTION

Flow cytometers have been in clinical and research use for many years and their applications in animal industry such as animal breeding industry has been rapidly increasing. A commercially available flow cytometer typically utilizes a cylindrical fluid geometry in its nozzle. This type of flow cytometer system has a focusing flow path with symmetry of revolution, as described in some U.S. patents (U.S. Pat. Nos. 5,602,039, 5,483,469, 4,660,971, 4,988,619 and 5,466,572). This type of design, according to the law of similarity, does not produce radially oriented samples. In clinical, animal breeding, and biological research fields, when cells such as sperm cells are sorted, they may be pre-stained with a dye that produces fluorescence when exposed to an excitation light source. As was explained in U.S. Pat. No. 5,135,759 to Lawrence Johnson, a flow cytometer that detects the emitted fluorescence perpendicular to the axis of flow can be used with high precision in the measurement and discrimination of the DNA content of the cells. However, as others have noted, even this precision in measuring the DNA content can only be achieved most efficiently when the cells of interest are spherical or cylindrical (Dean et al., 1978, Biophys. J. 23: 1–5). As for sperm cells—which have flattened heads—the observed fluorescence intensity depends largely upon the proper orientation of the heads with respect to the detector. Sperm cells emit a stronger fluorescent signal from the edge than the flat surface Therefore, the intensity of the fluorescent signal is dependent on the orientation of the sperm head as it passes the detector. Because DNA content is determined by fluorescence and because fluorescent intensity is affected by orientation, DNA content determination can be compounded by lack of orientation in a nozzle. For this reason, without radial orientation, the resulting fluorescence intensity distribution obtained for normal, randomly oriented sperm heads reflects both DNA content and head orientation. Because the cells emit a brighter fluorescence signal from the head edge (Gledhill et al., 1976, J. Cell Physiol. 87: 367–376; Pinkel et al., 1982, Cytometry 7: 268–273) the accuracy of DNA content determination (which may differ by as little as 3.5%) is highly affected by the cells orientation. For this reason, the conventional flow cytometer has experienced limitations, especially when sorting flattened sperm cells or other non spherical or non-cylindrical cells and the like.

Additionally, certain cells can exhibit decreased functionality as a result of the sort process. This can be particularly true for cells such as mammalian sperm cells which are not only mechanically delicate, but also which can become functionally impaired (as perhaps seen through reduced fertility) or even mortally wounded as a result of some occurrence in the sort process. For flow cytometry efforts with delicate cells there have been significant limitations on abilities. This is most acute in the highly specialized field of sperm cell sorting not only because the cells themselves are unusually delicate, but also because there is a need for extremely high sorting rates for physiological and practical reasons. These two competing needs have proven to pose uniquely critical challenges in the unique field of sperm sorting for commercial breeding purposes. Thus, while these two aspects—gentle handling and orientation—are perhaps independently applicable to a variety of instances, in many instances they can act synergistically. Both their independent characters and their synergistic interrelations are perhaps most acute in the commercial sperm sorting field. Interestingly, this synergy and potential interrelationship appears not to have been fully appreciated prior to the present invention.

Viewed in isolation, the aspect of proper orientation of a sample containing particles or cells can thus be seen to play an important role in the flow cytometer signal intensity and quality and in sorting efficiency. Efforts to hydrodynamically orient the sample have been made and the use of hydrodynamic orientation of the sample in flow through systems and flow cytometers have been explored in last few decades (Fulwyler, 1977, J. Histochem. Cytochem. 25: 781–783; Kachel et al., 1977, J. Histochem. Cytochem. 25: 774–780; Dean et al., supra). Hydrodynamic orientation of the sample within the flow cytometer can enhance precise measurement of relative DNA-stain content and can also provide a potentially useful measurement of morphological parameters such as cell thickness and degree of curvature of the flat face. For some applications, this orientation is straightforward. However, when delicate cells (such as sperm cells) or other particles are involved, however, a more gentle technique has been necessary. For example, a sample injection tube with a wedge shaped tip has even been used in some efforts to increase percentage of the oriented cells (Dean et al., 1978, Biophys. J. 23: 1–5; Fulwyler, 1977, J. Histochem. Cytochem. 25: 781–783; Johnson et al., 1986, Cytometry 7: 268–273; Pinkel et al., 1982, Cytometry 3: 1–9; Welch et al., 1994, Cytometry 17 (suppl. 7): 74). Because of the wedge shaped tip of the sample injection tube, the sample stream tended to be drawn into a thin ribbon by the sheath fluid as opposed to a cylindrical stream. Cells with flat heads such as mammalian sperm, often encountered the sheath fluid at a higher speed (100 mm/sec), and were then rotated so that their flat sides were in the plane of the ribbon. Unfortunately, the separation of the orientation event and the ultimate analysis event can cause less than optimal results. Therefore, this technique has not been practically shown to be as advantageous as desired.

In a different application, Kachel and his colleagues (Kachel et al., supra) demonstrated the law of similarity and discussed three types of flow paths that influenced the moving particles. They concluded that, to achieve uniform radial orientation with hydrodynamic forces for flat particles such as flattened red blood cells, the preferred flow path would be the one whereby unilateral constriction can be obtained. The most simple flow path that exhibits an increased unilateral constriction in use with a flow through system would be made of a tube with an ellipsoidal cross section, and would also end in an ellipsoidal outlet. In one arrangement, the long axis of this ellipsoidal outlet would be located at a right angle to the long axis in the cross section of the constricting elliptical tube. However, since the elliptical outlet does not produce the type of droplets desired for a high speed flow cytometer cell sorter, this arrangement was not intended to be used in, and has apparently not been applied to, a flow cytometer.

In a similar effort, Rens and his colleagues designed a nozzle tip that had an elliptical interior and an elliptical exit orifice (Rens et al., 1998, PCT Publication No. PCT/US98/15403; Rens et al., 1998, Cytometry 33: 476–481; Rens et al., 1999, Mol. Reprod. Dev. 52: 50–56). This interior contained a first ellipsoidal zone and a second ellipsoidal zone that were separated by a transitional zone. All the zones each had a long axis and a short axis. The long axis of the second ellipsoidal zone was oriented 90° to that of the first ellipsoidal zone. A cylindrical orifice, drilled through a jewel, was located at the end of the ellipsoidal exit orifice and served as the final exit. This device partially solved the problem of random orientation as existed in a conventional flow cytometer and could orient about 60% of the total flattened sperm cells from a boar each time through the flow cytometer. Nevertheless, when hydrodynamic forces in a flow path were taken into consideration, flat particles passing through the nozzle designed by Rens and his colleagues have received unnecessary stresses. For delicate cells, and especially for the perhaps more delicate sperm cells such as equine or bovine sperm cells, this approach simply did not appear to yield the desired efficiency either in orientation or in cell viability.

Thus, there existed a long felt but unsatisfied need for the invention while the needed implementing arts and elements had long been available. This need concerned the ability to gently handle and perhaps orient the particles or cells to be analyzed, the ability to properly analyze and sort efficiently, and the ability to minimize the potentially stressful situation that the flow cytometer caused for the particles or cells. Further, while problems existed in conventional flow cytometers, a full appreciation that a problem existed and what the problem was theretofore unseen by those skilled in the art. Substantial attempts by those skilled in the art to fill the need or to cope with the difficulties had been made but had not been fully successful most likely because of a failure to understand what exactly the problems were and perhaps how they interrelated. Some efforts made by those skilled in the art even matured into patents which seemed to have touched on the problems but, in fact, they tended in some regards to teach away from the technical direction in which the present inventors went.

SUMMARY OF THE INVENTION

It is therefore the object to present an improved nozzle interior surface geometry that produces the simplest flow path for applying necessary hydrodynamic forces to accelerate and perhaps orient a sample into a proper direction for analyzing and efficient sorting purposes. This improved nozzle interior surface geometry can comprise either or both of: an appropriately configured accelerative force feature and/or an elliptical-like, single torsional interior surface element within a single torsional orientation nozzle that produces the special hydrodynamic forces, namely, single torsional orientation forces.

As the present invention now shows, the problems with undesirable cell stress could be viewed as at least in part due to either inappropriate handling forces, specifically: inappropriate accelerative forces, or the existence of a second torsional force created by the second ellipsoidal zone. As to the accelerative forces applied, devices often utilized abrupt transitions internal to the nozzle and so caused extreme acceleration over short distances. As to the orientation aspect, for example, approaches such as that of Ren (mentioned earlier) showed, that after cells had been oriented by a first torsional force created by a first ellipsoidal zone, an additional—perhaps doubling—stress was applied. Specifically, the flat particles were already in an oriented position after they were oriented from a random position by the first ellipsoidal zone. They were ready to exit in oriented positions. At this time, however, the devices of Rens and others unnecessarily twisted these oriented flat particles a second time by the hydrodynamic forces created by a second ellipsoidal zone. As the present invention shows, these designs are not fully efficient in a high speed flow cytometer. When flat sperm cells with tails are oriented through this type of the nozzle, besides its inefficiency, the geometry in this type of the nozzle apparently impacts twice the torsional forces. This appears to unnecessarily and highly stress or damage the long tailed sperm cells before they exit the nozzle. In addition, in some designs where the orifice is made of a jewel that is separate from the main interior, a smooth laminar flow can also be affected to some degree. This could cause almost instantaneous acceleration and so could unnecessarily stress the cells and could affect the orientation of the already oriented sperm cells. Therefore, the approaches of Rens and other more recent efforts actually teach away from the more efficient, less accelerative and less torsional and smooth laminar interior surface of an embodiment of the present invention.

It is another object to design the simplest nozzle interior surface geometry that provides laminar flow surface and at the same time that reduces the distortion of the sample, especially of sperm cells.

Yet another object is to present a system which can more quickly and more accurately measure and sort the sample, especially delicate sperm cells in research and clinical use and in the animal insemination industry.

A further object to provide methods for improving orientation and sorting efficiency of the sample, especially the sperm cells in the flow cytometry for research and clinical use and animal insemination industry.

Naturally, further objects of the invention are disclosed throughout other areas of the specification and claims.

BRIEF DESCRIPTION OF THE DRAWINGS

FIGS. 3A, 3B, and 3C are schematic drawings of one of the present embodiments of the nozzle. FIG. 3A is a three-dimensional view of the nozzle tip showing the first ellipticity-increasing zone, the desired ellipse demarcation location, the ellipticity-decreasing zone, the conical zone, the cylindrical zone, and the circular exit orifice. FIG. 3B is a schematic cross sectional view showing the tapered interior surface of the nozzle in a unitary design. FIG. 3C is a cross sectional view of the cylindrical zone and the circular exit orifice.

FIG. 6 is a schematic diagram of an example of a nozzle having axial motion surfaces as may have existed in the prior art.

FIGS. 7a, 7b, and 7c are plots of the theoretical axial velocity, acceleration, and rate of change of acceleration motions with respect to location as may exist for a nozzle such as that shown schematically in FIG. 6.

FIG. 8 is a schematic diagram of an example of a nozzle having axial motion surfaces according to one embodiment of the present invention.

FIGS. 9a, 9b, and 9c are plots of the theoretical axial velocity, acceleration, and rate of change of acceleration motions with respect to location as may exist for a nozzle such as that shown schematically in FIG. 8.

DETAILED DESCRIPTION OF THE PREFERRED EMBODIMENTS

Figure 1:
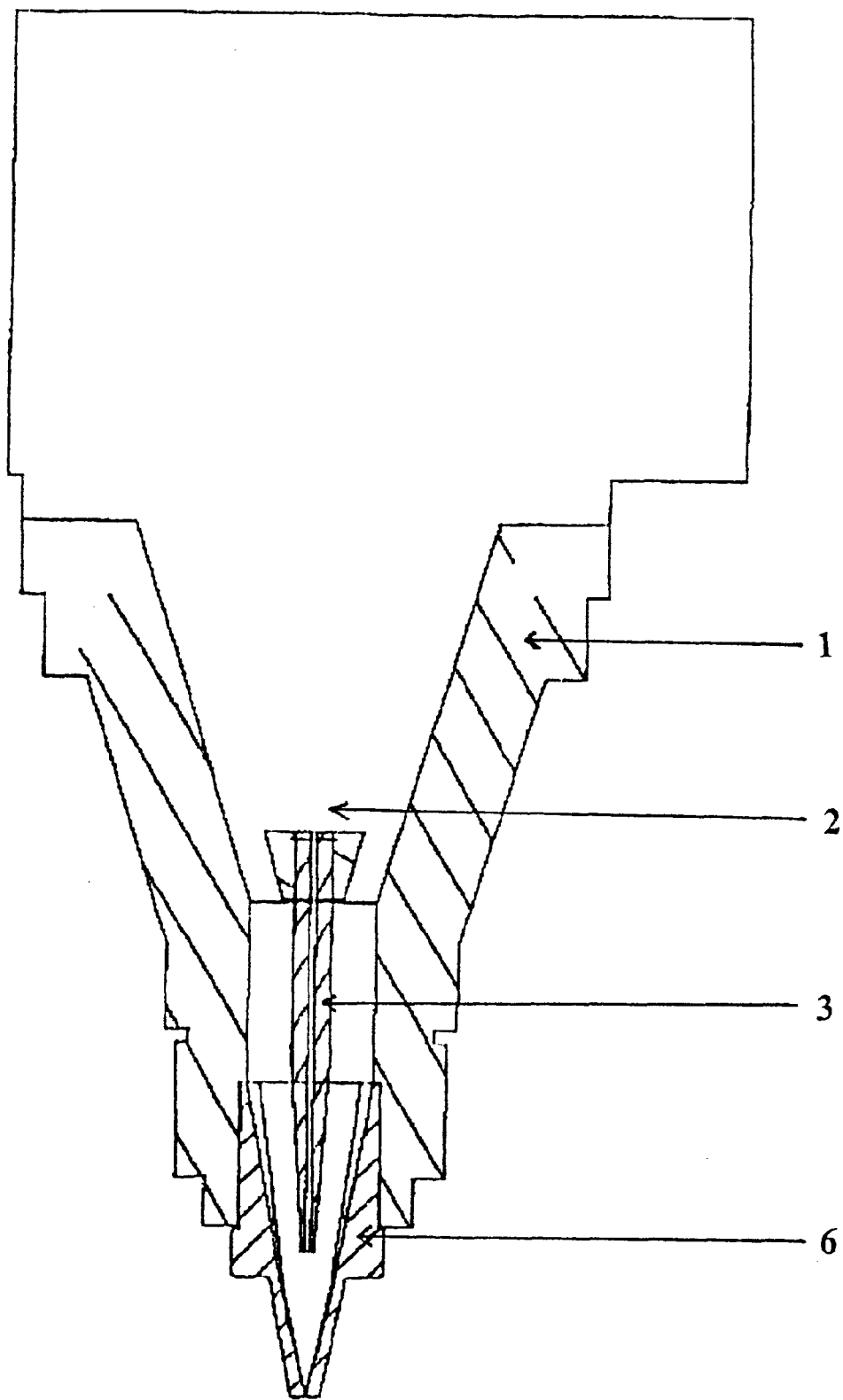
FIG. 1 is a cross sectional view of a portion of a flow cytometer showing a sheath fluid container, a sample injection tube and a nozzle of the present invention. This figure also shows a relative location of the sample tube within the nozzle.

As can be seen from the illustrations and in keeping with the objects of the present invention, the basic concepts of the present invention can be implemented in different ways. Referring to FIG. 1, it shows a portion of a flow cytometer system where a sample is processed into individual droplets prior to being analyzed and sorted. As is well understood by those having ordinary skill in the art, from the schematic cross sectional view, a sheath fluid container (1) may contain some sheath fluid (2) imported through a sheath fluid port (not shown). A sample injection system comprises a sample injection tube (3) connected to a sample reservoir (not shown). The sample injection system generally acts to provide the appropriate flow of some sample material to a nozzle system. The sheath fluid container at the same time introduces a sheath fluid into the nozzle system. The sample may be surrounded by the sheath fluid to form a sample-containing fluid and may then exit the nozzle system through a drop-forming mechanism through which the sample-containing fluid forms small droplets. These small droplets may pass through a free falling area at a high speed of over about 20 meters per second by combination of oscillation by an oscillator and high pressure from the flow cytometer system. Subsequently, these small droplets, i.e., the sample-containing drops, may be analyzed by an analytical system (not shown) at the free falling area. If living cells such as flat sperm cells are introduced as the sample material, they may be stained with one or more fluorescent dyes. These sperm cells may be carried in single file in the sheath fluid stream past the analytical system (not shown). The analytical system may include a focused laser whose wavelength is adjusted to excite a fluorescent dye that may be present. The fluorescence signal collected from each cell can then be sensed through a detecting system (not shown). Then, this process may include a sorting process by a sorting device or the like, depending on the individual physical property such as the DNA content of each cell introduced, through the differential application of charge to the various droplets as those skilled in the art readily understand. Subsequently, each cell is sorted depending on its charge. As mentioned earlier, these general aspects of flow cytometry are well known and are discussed in the references mentioned earlier (hereby incorporated by reference).

In relation to the handling of the sample for the flow cytometer's functions and the sample's viability, two aspects can be important: torsional alignment and the sample's axial motion. Each of these is discussed separately, however, it should be understood that they are not mutually exclusive and can synergistically have effects. This is especially true as it relates to the sample's viability, that is, the ability of the sample to perform its functions with efficacies expected and not substantially affected by the flow cytometry processing. The first of these two aspects, torsional alignment, is discussed first.

Figures 2, 2A:
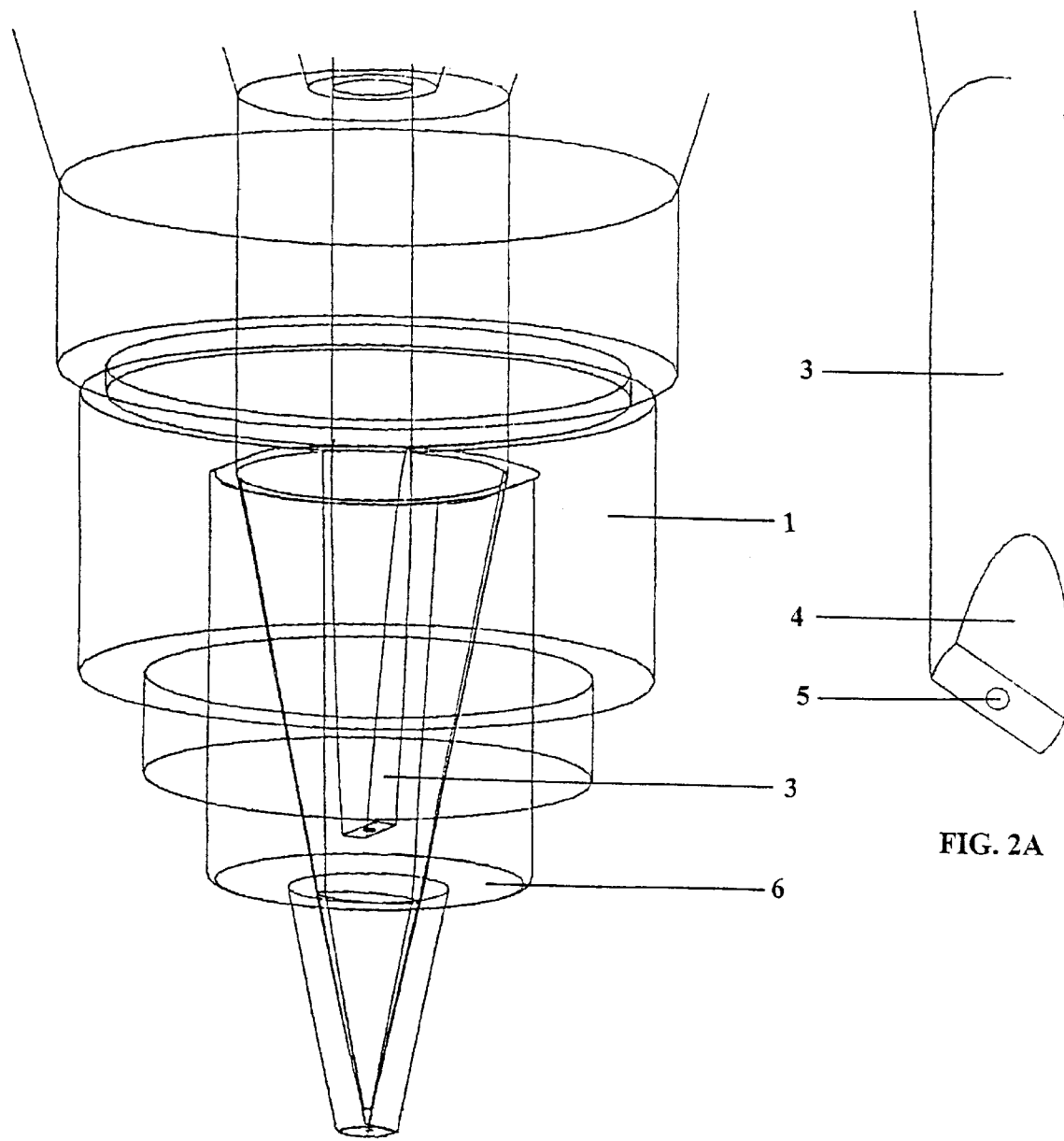
FIG. 2 is a three-dimensional view of one nozzle tip and its relative position with the sheath fluid container (here the nozzle body) with a sample injection tube and a nozzle tip.
FIG. 2A is a schematic drawing of the sample injection tube that has a beveled tip and a circular mouth.

The aspects illustrated in FIG. 1 can also be seen through the three-dimensional view shown in FIG. 2. This three dimensional view shows a portion of the flow sheath container (2), the sample injection tube (3) and the nozzle system having a nozzle (6). The sample injection tube (3), as shown in FIG. 2A in detail, has a beveled tip (4) and a circular mouth (5). The specially designed nozzle (6) is termed a single torsional orientation nozzle in the present invention and will be presented in detail below.

As is known, the sample injection tube serves to introduce the sample material in thin flow into the nozzle system where the sample is surrounded by the sheath fluid. As is well known for those having the ordinary skill in the art, the conventional sample injection tube often has a cylindrical shape. However, since this type of sample injection tube may not help in controlling orientation of the sample, the sample coming out from this type of the sample injection tube usually has a non-oriented status. In last a couple of decades, a modified sample injection tube was produced (Dean et al., 1978, supra; Fulwyler, 1977, supra; Johnson et al., 1986, Cytometry 7: 268–273; Pinkel et al., 1982, supra). This modified sample injection tube may have a beveled tip and can help, to some degree, in orienting the sample material coming out of its tip. Because of the beveled shape at the tip of the sample injection tube, the sample stream can be drawn into a thin ribbon by the sheath fluid. The resulting change in flow condition can cause a corresponding orientation of the sample material.

In the present design, based upon the concept of the mechanism of the beveled tip, the sample injection tube with the type of beveled tip shown is maintained but the specific interior size is unique. Most important, the location of the beveled tip within the nozzle is especially established. As shown in FIG. 2A, the sample injection tube (3), termed here an orientation-improving sample injection tube, comprises a beveled tip (4) and a circular mouth (5) in its cross section. The beveled tip is more or less a rectangular shape in its cross section. This has a long axis and a short axis. While naturally this may be varied to suit the application or the particles being sorted, in one preferred embodiment the angle of the beveled tip is about 4°, the outer diameter of the tube is about 1.5 mm and the diameter of the circular mouth is about 0.25 mm.

By this far, we have only discussed the role a sample injection tube plays in orienting the sample. It can be understood that, however, as those skilled in the art should understand, the orientation forces provided in this manner are very limited. For example, had this feature alone solved the orientation problems, the efforts thereafter on high percentage orientation would not have been necessary. Instead, as those skilled in the art realized, to get a highly oriented sample, especially when the sample contained the flat, non-spherical, or delicate cells such as sperm cells for an insemination purpose or the like, an additional approach was necessary. As the present invention shows, the majority of the orientation forces should come from the interior surface of the nozzle. Thus, the nozzle served as a fundamental element for the production of functional, and appropriately powerful yet gentle orientation forces.

With this understanding, it can now be seen how the present design differs in one regard from the prior art. As can be seen from FIGS. 1 and 2, and as particularly called out in FIGS. 3A, 3B, and 3C, the flow cytometer system comprises the uniquely designed single torsional orientation nozzle (6). The single torsional orientation nozzle (6) may be made of some selective Is materials such as a ceramic material and the like. Although the size of the nozzle, e.g., the height and the diameter, etc., may be varied, it should preferably fit into a conventional flow cytometer and at the same time provide the desired orientation forces as described in this present invention. Further, although in one preferred embodiment the nozzle is made into a single piece, for the purpose of a better illustration, it may be divided into two portions, i.e., an upper cylindrical portion (a) and a lower conical portion (b). In one of the preferred embodiments, the height of the upper cylindrical portion (a) may be about 8 mm and the outer diameter may be about 6 mm. The height of the conical portion (b) may be about 4.5 mm and the outer diam at the orifice may be less than about 1 mm. Thus, the total height of the nozzle may be about 12.5 mm. The use of a unitary nozzle also aids in fixing all orientation and axial motion factors in an optimum arrangement. It can thus increase ease of use, repeatability, and other practical matters as well.

FIG. 3A is a three-dimensional view and FIGS. 3B & 3C are schematic cross sectional views of a single torsional orientation nozzle of the present invention. As can be best illustrated in FIGS. 3A and 3B, The single torsional orientation nozzle (6) comprises a nozzle volume enclosed by an interior surface element. The interior surface element of the single torsional orientation nozzle constitutes its interior geometry. The interior surface element may comprise a single torsional interior surface element having a single torsional interior surface. This single torsional interior surface element has the ability of generating single torsional hydrodynamic forces having a hydrodynamic axis when a flow containing the sample passes through it. The single torsional interior surface element also has a velocity accelerating characteristic that may produce an accelerating velocity upon the sample. When the sample passes through this single torsional interior surface element, the sample may be oriented by the single torsional hydrodynamic forces and radially aligned with respect to the hydrodynamic axis. It may also be accelerated to exit for the subsequent analysis and sorting process. These special single torsional hydrodynamic forces may be referred to as single torsional orientation forces.

The overall shape of the single torsional interior surface is gradually tapered downstream so it may be referred as a gradually tapered, single torsional interior surface element. From the longitudinal section view as shown in FIG. 3B, this gradually tapered, single torsional interior surface element may be viewed in two dimension as being a "fan-like" shape that opens from the bottom to the top. The tapered degree of the gradually tapered, single torsional interior surface element may vary but may preferably be about 23° from the bottom of the "fan-like" shape to the top so that the desired accelerating force may be generated to act upon the sample. In addition, the gradually tapered, single torsional interior surface element may be divided into a few zones based upon its interior geometry and each zone may have a laminar flow surface. Basically, the gradually tapered, single torsional interior surface element may be made of a tapered, elliptical-like interior zone (c) having an elliptical-like, single torsional interior surface and a cylindrical interior zone (d) in the three-dimensional view. This elliptical-like, single torsional interior surface may include different shapes in its cross sections. For example, besides being ellipse-shaped, it may be oval-shaped, or even close to a rectangle-shape. Any of these shapes may occur at any location along the elliptical-like, single torsional interior surface just above and below a demarcation location at which its ellipticity, ovality, or even rectangularity reaches a maximum or desired degree. As should be understood, each of these shapes is intended to be encompassed by the term "elliptical-like" even though a true mathematical ellipse is not present at a given cross section. Similarly, where discussed, the term "circular" need not be perfectly circular—or even circular at all. Again, it may be preferred to be circular, however, other shapes may be equivalent so long as the appropriate function is present.

Of course, the tapered, elliptical-like interior zone may have a major axis and a minor axis in its cross sections and the ellipticity may be smoothly controlled. Thus, depending upon its ellipticity variation, this tapered, elliptical-like interior zone may be divided into the following zones from the top downstream to the bottom:

1) an ellipticity-increasing zone (8) with a circular mouth (7) at the top wherein the ratio of the major axis to the minor axis in the cross sections is increasing;
2) a desired ellipse demarcation location (9) downstream the ellipticity-increasing zone (8) at which the major axis to the minor axis reaches an optimal ratio that may be a maximum ratio for a sample as can be best illustrate in FIG. 3A; and
3) an ellipticity-decreasing zone (10) wherein the ratio of the major axis to the minor axis in the cross sections is decreasing.

Based upon the above described geometry, the two dimensional shapes of the cross sectional view from the top to the bottom of the tapered, elliptical-like interior zone may undergo transitional changes from a circle at the mouth region, to elliptical-like shapes (which may even be actual ellipses) with gradually increasing ellipticity (that is the ratio of major to minor axes—regardless of the shape involved), to the desired ellipse or the like, to elliptical-like shapes with gradually decreasing ellipticity, and finally to a circle again at the region where the tapered elliptical-like interior zone joins the cylindrical zone. Since the whole elliptical-like interior zone is tapered, the cross sectional areas of the whole elliptical-like interior zone will become gradually smaller from the top to the bottom. The ellipticity may thus be adjusted by changing the ratio of the major to the minor axis. The major to the minor axis ratio may gradually change from the top from 1 to larger than 1, or perhaps even an optimal ratio for the sample. The optimal ratio may be a maximum ratio. Subsequently, the ratio may gradually change back from the maximum ratio to smaller than the maximum ratio and then to 1. As those skilled in the art may well know, when the ratio becomes 1 the shape in cross section may be a circle. The maximum ratio as referred above may vary to some degree. In a preferred embodiment, the length of the major axis may be 2.2 mm and that of the minor axis may be 1.0 mm. Thus, the maximum ratio is designed to be about 2.2 for this one preferred embodiment. Naturally it may vary based on application or the like.

In one embodiment, the desired ellipse demarcation location (9) downstream the ellipticity-increasing zone (8) within the nozzle may be the place where the beveled tip of the sample injection tube is located. This may also be the place where the sample in the ribbon flow receives desired orientation forces that are fully functional, where the sample is minimally torqued by the desired orientation forces or torquing forces, where the time required for cell to exit is minimal, or where the sample after exiting from the orifice of the nozzle can still well maintain its oriented status so the subsequent analysis and sorting can be conducted efficiently.

This location may be referred as an injection point. For the current state-of-the-art high speed sorting flow cytometer now operated, this location or the injection point, based on the discoveries of the present invention, may be about 6 mm from the exit orifice. Thus, if an orientation maintaining distance is defined as the distance that indicates how far a sample particle can maintain its oriented status from the point at which it is oriented to a point at which it statistically loses its degree of oriented status, the distance from the beveled tip of the sample injection tube to the exit orifice of the nozzle and the distance from the exit orifice to the intersection with the laser beam or sensor along the flow path in the falling zone well falls within this orientation maintaining distance. For example, it may be within 10 mm from the beveled tip to the intersection with the laser beam, as described by Dean and his colleagues (Dean et al., supra). Therefore, any sample particles that are oriented, no matter at which point within the distance from the beveled tip to the intersection with the laser beam or sensor, will maintain their oriented status before they are analyzed. Theoretically, this orientation maintaining distance could even be longer than 10 mm when a flow cytometer is equipped with the specially designed nozzle of the present invention and the sample injection tube with the beveled tip. Further, for the full orientation benefits, the long axis of the beveled tip may be aligned with the major axis of the desired ellipse demarcation location and short axis is with the minor axis as shown.

Downstream from the tapered, elliptical-like interior zone (c) may be a cylindrical interior zone (d). This cylindrical interior zone (d), as can be seen in both FIGS. 3A, 3B, and 3C may be further divided into a conical zone (12) that is tapered and a cylindrical zone (14). The conical zone (12) has a larger circular mouth (11) at the top that joins with the tapered elliptical-like interior zone (c) and a smaller circular orifice (13) in connection with the cylindrical zone (14). The larger circular mouth (11) at the top of the conical zone may be about 0.19 mm in diameter and the circular opening may be about 0.07 mm in one preferred embodiment. The height of the conical zone may be about 0.3 mm. The cylindrical zone (14) may also have a mouth with the same diameter as the smaller opening of the conical zone throughout its circular exit orifice (15) and may be about 0.15 mm in height.

Figure 4B:
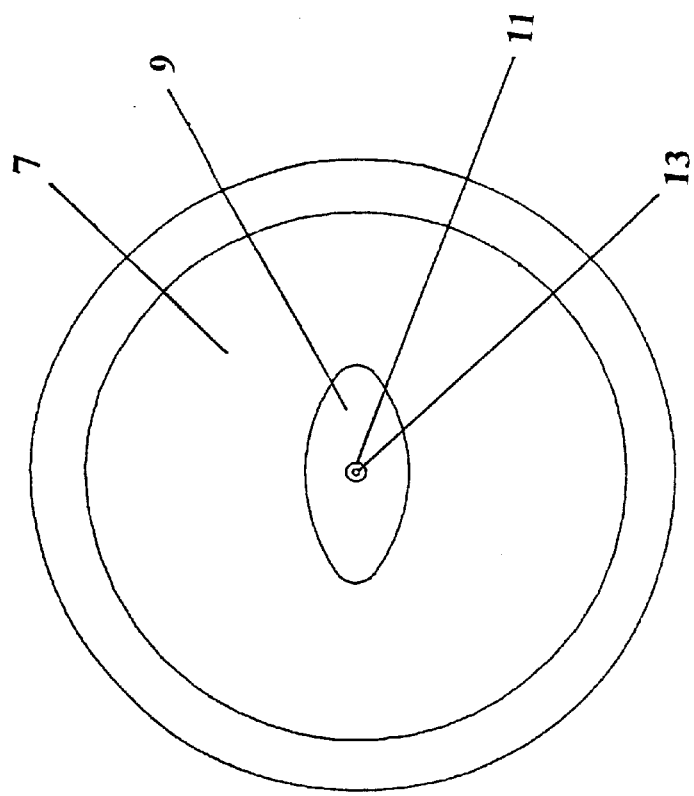
FIG. 4B is a top view of the interior design of the nozzle showing the largest circular mouth, the desired ellipse demarcation location, the larger circular mouth of the conical zone and the smallest circular mouth of the cylindrical zone. The diameter of the smallest mouth is also that of the circular exit orifice.
Figure 4A:
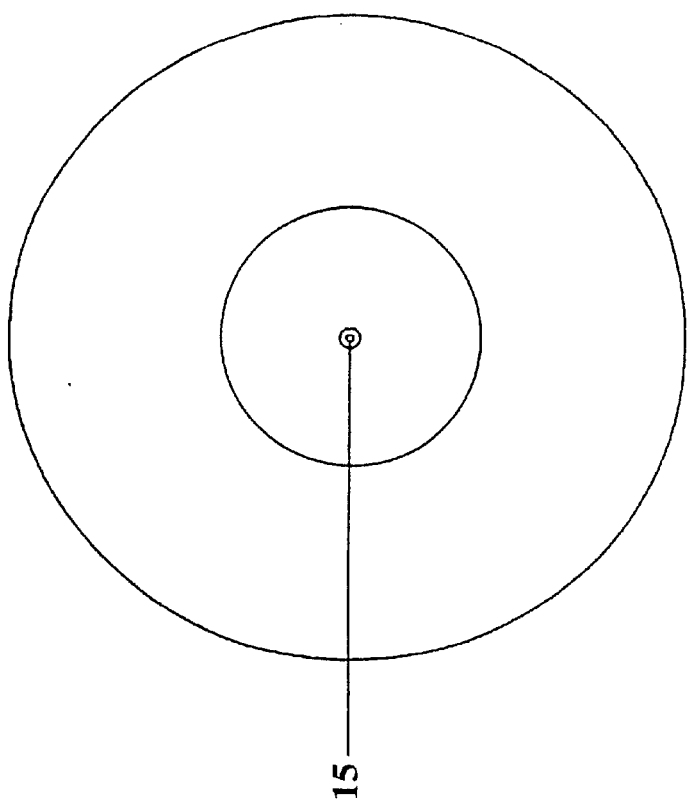
FIG. 4A is a bottom view of the nozzle tip region showing specifically the circular exit orifice.

FIG. 4A illustrates a bottom view of the single torsional orientation nozzle showing the circular orifice. The circular orifice should be small enough so that tiny droplets containing sample particles may be formed. The diameter in one of the preferred embodiments may be about 0.07 mm. FIG. 4B shows a top view of the single torsional orientation nozzle. As can be seen clearly, the mouth may be in a circular shape with a diameter of about 5.25 mm.

Figure 5:
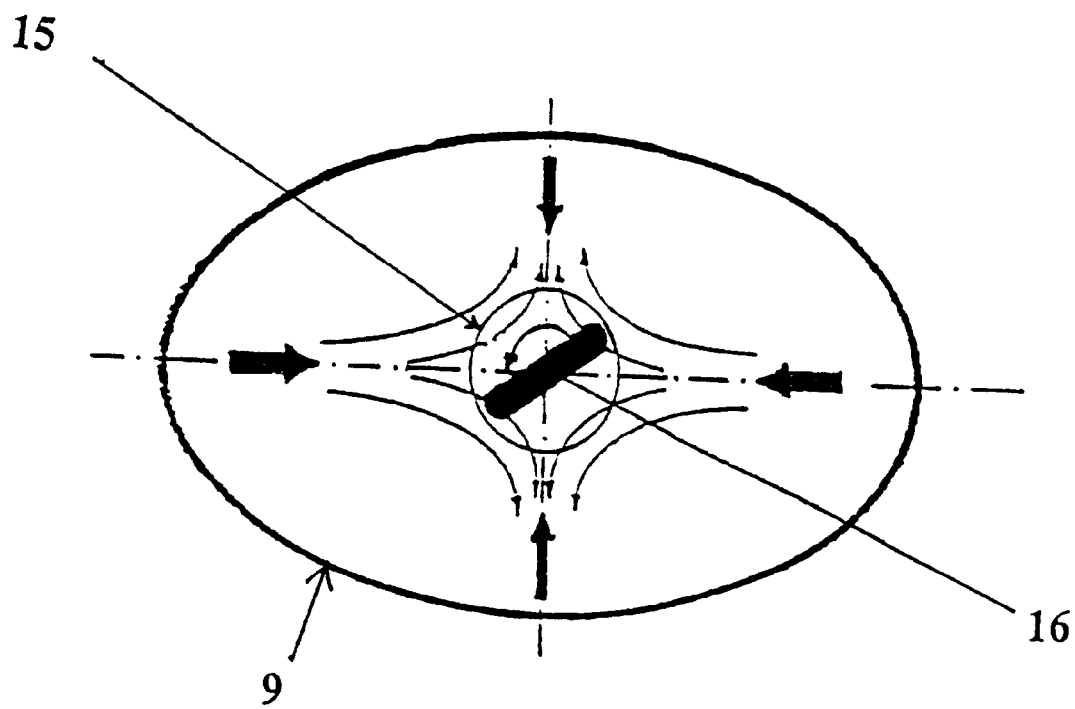
FIG. 5 shows how the single torsional orientation nozzle works in orienting flat particles.

Referring to FIG. 5, it can be seen how orientation occurs. As may be noticed, this figure is a modified drawing from Kachel and his colleagues (FIG. 3, Kachel et al., 1977, J. Histochem. Cytochem. 25: 774–780). This drawing, a cross section around the desired demarcation ellipse location (9), shows, first of all, the distributions of the orientation forces generated from the elliptical-like, single torsional interior surface. As shown, the dissimilar transformation of the elliptical-like, single torsional interior surface can cause preferential side forces to generate additional flow components along the major axis and may decrease the forces generated along the minor axis. Thus, the forces generated along the major axis may be viewed as stronger than the forces generated along the minor axis to thus orient a flat particle (16) as shown. The unique design of the present invention shows its superiority in that the tapered, elliptical-like interior zone (c) is connected directly to the cylindrical interior zone (d) and the circular exit orifice (15). This specially designed geometry successfully avoids the law of similarity and, therefore, the sample particles that have been oriented will be able to individually exit the circular exit orifice and still maintain their orientationally aligned status.

In addition to the above, the whole tapered, single torsional interior surface element may be viewed to comprise a laminar flow surface. Through a laminar flow and the single torsional orientation forces generated by the laminar flow surface, the sample may be radially oriented and aligned along the hydrodynamic axis. The orientationally aligned sample is thus maintained at the orientationally aligned status when exiting the circular exiting orifice where the sample is split into individual particles and the like, is surrounded by a sheath fluid drop, and is analyzed. Therefore, the finally oriented sample can be due to the combined efforts from the beveled tip of the sample injection tube and the single torsional orientation interior surface that, because of the unique geometry, generates single torsional orientation forces and produces laminar flow.

It has to be pointed out that the whole interior surface of the single torsional orientation nozzle may be unitary. The way of dividing the whole interior surface into the tapered, elliptical-like interior zone (c) the cylindrical interior zone (d) and their own subsequent zones as described above is purely for a clear explanation purpose.

The animal breeding industry has been increasingly taking advantage of the principles of flow cytometry and utilizing the benefits that a high-speed flow cytometer can provide. Sexed sperm specimens can now be successfully discriminated by the sorting mechanisms that the flow cytometer employs. With this uniquely designed single torsional orientation nozzle, the X and Y-chromosome-bearing sperms may be sorted more efficiently and at a higher percentage as described above. Sexed sperm cells may be buffered in our specially prepared sperm compatible buffer as described in PCT Publication No. WO 99/05504 (LoDo PCT). The buffered sperm cells may be injected at the demarcation location within the elliptical-like, single torsional interior surface element of the single torsional orientation nozzle where they may be surrounded by the sheath fluid to form a sheath-surrounded sperm. Subsequently the sperm-containing drops may be produced by a drop-forming mechanism and analyzed at the free falling area. The sperm-containing drops are then charged and sorted by the sorting device and colleted by a sperm-compatible collecting system containing a specially made sperm-collecting fluid. This whole process may minimize the stresses upon the sperm created through the sorting process. The X or Y-chromosome-bearing sperm may then be used for insemination and production of a mammal of a desired sex.

Thus, it is at least the unique design of an interior surface geometry of the single torsional orientation nozzle that makes the invention superior to other conventional nozzle. As will be well expected by those having ordinary skill in the art, this single torsional orientation nozzle, when specially combined with the beveled sample injection tube located at an appropriate location relative to a specific region of the interior surface of the single torsional orientation nozzle, can provide results which may be even more satisfactory.

As mentioned earlier, the forgoing discussed the torsional alignment aspect of the invention. A second important aspect is that of the sample's axial motion. This aspect encompasses not only the motion of the sample as it traverses the nozzle down the central axis, but the stresses the sample receives during its path. These motions can perhaps be most easily characterized by three values, the three derivatives of distance with respect to location along the sample. These derivatives can be summarized by the following:

| Derivative | Analogous more Common Concept |
|---|---|
| first derivative of distance with respect to location | velocity |
| second derivative of distance with respect to location | acceleration |
| third derivative of distance with respect to location | rate of change of acceleration |

As may be understood from FIGS. 6–9c, the nozzle may present any number of axial motion surfaces, that is surfaces which influence or perhaps only confine the sample as it passes through the nozzle. As shown in FIG. 6, the axial motion surfaces may be symmetric pairs and may also be as simple as a first axial motion surface (21) and a second axial motion surface (22). As the sample passes down the nozzle (6), these axial motion surfaces can act in manners which influence the sample or its viability. The sample is thus (usually hydrodynamically) subjected to a first axial motion surface (21). It may then transition at a transition location (23) to become influenced by a second axial motion surface (22). After the transition location (23) the sample is then subjected to the second axial motion surface (22). It may then exit the nozzle such as at the circular exit orifice (15).

It should be understood that the axial motion surfaces can have any shape. In a system, such as one that may have constant velocity, they may have a tubular shape. As shown in FIGS. 6 & 8, in a system such as one that achieves acceleration of the sample as it passes through the nozzle (6), they may be configured as acceleration surfaces such as the conical surfaces shown. The acceleration surface could also decelerate the sample, of course. By causing acceleration or deceleration, the surface would at so as to change the velocity of the sample as it passes through the nozzle (6). Thus, it can be understood that the nozzle (6), such as shown in FIG. 8 may include a first axial acceleration surface (24) and a second axial acceleration surface (25). The first axial acceleration surface (24) causes the sample to experience an a first acceleration value (which may or may not be constant) and the second axial acceleration surface (25) can cause the sample to experience a second acceleration value. This second acceleration value may or may not be different from the first. As shown in FIG. 8, since the second acceleration surface (25) converges at a different rate, it likely would indicate a different acceleration value.

Naturally, anytime there is an acceleration, the sample may experience a stress. This stress can have impacts on the samples viability and functionality. One particular aspect for some samples, such as longer cells, may be the fact that when there is a change in velocity, there may be differences in the velocity tendency from one end of the sample to the next. This may be most easily understood in reference to a sample such as a sperm cell. Viable sperm cells have heads and tails. When the head is accelerated differentially from the acceleration of the tail, or when the head is moved at a velocity different from that of the tail, a differential may be created from head to tail. This differential may cause stress on the cell. In extreme cases, it may even pull the tail from the head. Obviously this could destroy the efficacy of the sample. The present invention provides a system through which this can be minimized and the undesirable effects can be avoided or reduced. This is accomplished by subjecting the sample to a "low" degree of changes in acceleration or velocity across the sample's length. As those in the art would be able to understand, "low" may be a relative term which can depend on the cell and the environment. It may be theoretically or empirically determine as a value which is shown to achieve practical percentages of efficacy in the sample for its specific application. These probabilities may be such as at least 70%, 80%, 90%, or the like. The "low" acceleration or rate of change in acceleration may also be affirmatively applied.

Changes in acceleration or velocity can occur when the axial motion surfaces change. These changes can be abrupt or gentle. Naturally some embodiments of the present invention prefer the latter. Referring to FIG. 6, it can be seen how an abrupt change in the axial motion surface along the axis can stress the sample. The first axial motion surface (21) changes in a discrete fashion at the transition location (23). For example, when the second axial motion surface (22) is created by a separate element, such as by the insertion of a jewel, there can exist a discontinuity in the nozzle (6). At such a point, the sample can then be subjected to an extreme change in velocity almost instantaneously. Note that such a discrete change may exist unintentionally, due to almost imperceptible misalignments. Regardless, aspects such as these can tend to pull the sample apart. By providing transitions which may not be discrete the present invention can avoid or minimize the stresses thus created. The transition can be a continuous transition as in curved area, by having a limited amount of 'discreteness' or misalignment, or may just avoid the possibility of a discrete change by having an inner surface on the nozzle (6) which is unitary. In this manner, the nozzle may effectively have a unitary surface. In such an arrangement, the nozzle (6) can be affirmatively designed so as to present a transition with a maximal acceleration differentiation. As shown in FIG. 8, this may be done through designing in a limited maximal acceleration differentiation transition area (26) such as shown between the first axial motion surface and the second. It may also be accomplished by using a unitary exit orifice. The limited maximal acceleration differentiation transition area can then be at or as a result of the unitary exit orifice.

In terms of the three derivatives of distance with respect to location mentioned earlier, the above concepts can be understood by reference to FIGS. 7 *a*–*c* and 9 *a*–*c*. As shown, these figures are graphical representations of the three derivative values at respective locations in their adjacent nozzles shown in FIGS. 6 & 8. FIGS. 7*a* and 9*a* represent the first derivative of distance with respect to location, a concept similar to velocity. Since the nozzle in FIG. 6 has a discrete change at the transition location (23), it can be seen that dl/dl changes discretely at the transition location (23). For the nozzle (6) in FIG. 8, the dl/dl value does not discretely change. This the sample may be treated to less stress for this reasons alone. In FIGS. 7*b* and 9*b*, it can be seen that the $d^2l/dl^2$ values for their respective nozzle are also different. In FIG. 7*b*, the second derivative of distance with respect to location value (or perhaps more easily viewed as acceleration) has a moment of extreme change. Again, this is not so present in FIG. 9*b*. Finally, the third derivative of distance with respect to location values, $d^3l/dl^3$, (or perhaps more easily viewed as rate of change of acceleration) also differ. In FIG. 7*c*, the value first goes positive and then negative. In the values shown in FIG. 9*c*, the values never change signs, they are either zero or positive, but never negative. Each of these concepts can be conveniently constructed through which to understand and characterize the nozzle as it is designed to avoid or minimize stresses on the sample.

An other aspect which may be a factor for some samples is the aspect of the duration of the velocity, acceleration, or rate of change of acceleration as experienced by the sample. This may also be referred to as the dwell time for the sample. In flow cytometry, there is often a need for single samples to be placed in single drops. Aspects such as this can cause a desire to transition the fluid at the last possible time. In systems which attempt to do this, it can be important to pay particular attention to areas in the vicinity is about 100 um of the exit point (27), areas more than 300 um away from the exit point (27), areas in the vicinity of the exit point (27), or even areas away from the exit point (27). In addition, in some systems it may be acceptable to only momentarily subject the sample to the undesired values. Thus limits can be established throughout the nozzle (6) or at specific locations within the nozzle (6). Some of the limits which can be applied are set forth in table s 1 & 2.

TABLE 1

| $d^2l/dl^2$ values | |
|---|---|
| 0.16 m/sec per micron in the nozzle, | $100 \times 10^{-3}$ m/sec per micron at a distance of more than 300 um away from the exit point, |
| 0.05 m/sec per micron in the nozzle, | $50 \times 10^{-3}$ m/sec per micron at a distance of more than 300 um away from the exit point, |
| the above values away from the vicinity of the exit point, | $25 \times 10^{-3}$ m/sec per micron at a distance of more than 300 um away from the exit point, |
| 0.10 m/sec per micron away from the exit point, | values which do not discontinuously change along a central axis, |
| 0.13 m/sec per micron away from the exit point, | values which are at most any of the above, |
| 0.16 m/sec per micron in the vicinity of the exit point, | any of these values at various locations, |
| 0.20 m/sec per micron in the vicinity of the exit point, | any combination of these values, |
| 0.23 m/sec per micron in the vicinity of the exit point, | any combinations of any of these values with any of the values in Table 2. |

TABLE 2

| $d^3l/dl^3$ values | |
|---|---|
| $100{,}000 \times 10^{-6}$ m/sec per micron$^2$ in the nozzle, | $200 \times 10^{-6}$ m/sec per micron$^2$ at a distance from the exit point, |
| $10{,}000 \times 10^{-6}$ m/sec per micron$^2$ in the nozzle, | $100 \times 10^{-6}$ m/sec per micron$^2$ at a distance from the exit point, |
| $2{,}000 \times 10^{-6}$ m/sec per micron$^2$ in the nozzle, | a rate of change of acceleration values with respect to axial location as do not discontinuously change in the nozzle, |
| $1{,}100 \times 10^{-6}$ m/sec per micron$^2$ in the nozzle, | a rate of change of acceleration values or $d^3l/dl^3$ values as do not change sign in the nozzle, |
| the above values away from the vicinity of the exit point, | values which are at most any of the above, |
| $100{,}000 \times 10^{-6}$ m/sec per micron$^2$ away from the exit point, | any combination of the above values at various locations, |
| $50{,}000 \times 10^{-6}$ m/sec per micron$^2$ away from the exit point, | any combination of the above. |
| $10{,}000 \times 10^{-6}$ m/sec per micron$^2$ away from the exit point, | any of these values at various locations, |
| $5{,}000 \times 10^{-6}$ m/sec per micro$^2$ away from the exit point, | any combination of these values, |
| $1{,}000 \times 10^{-6}$ m/sec per micron$^2$ away from the exit point, | any combinations of any of these values with any of the values in Table 1 |
| $300 \times 10^{-6}$ m/sec per micron$^2$ away from the exit point, | |

In affirmatively coordinating such aspects with specific samples, the values may also be established over the effective cell/sample length. These lengths can be both theoretically determined, measured as the actual sample length, or even be empirically determined as an effective sample length. Again, these affirmative or coordinated actions result in avoiding leaving things to chance and can permit certainty for users. In the empirical determinations, among others, it should be understood that the values achieved may be chosen so as to not exceed the practical capabilities of the sample over its length, that is so that the sample retain a sufficiently acceptable probability of functionality after they are processed. In these manners, by coordinating the maximal acceleration differentiation, by affirmatively limiting the maximal acceleration differentiation, and by affirmatively choosing values (determined or not) so as to not exceed the practical capabilities of the sample, the present invention can achieve its ends.

As mentioned earlier, synergy can exist between this aspect and the hydrodynamic alignment aspect of the invention. The combined twist and pull can and apparently does cause stress in some samples, especially sperm cells. Thus the possibility of combining the torsional hydrodynamic forces and the maximal acceleration differentiation or the like values, these aspects can combine to minimize stress as well. There can also be considered the aspect of combining the above values and concepts with other parameters which are likely to cause stress in a flow cytometer setting. Such parameters may include operation at sort rates of at least 500 sorts per second, at least 1000 sorts per second, and at least 1500 sorts per second. Similarly, this can also include operations at 50 psi and the like. Finally, as alluded to above, certain samples can particularly susceptible to stress, to the aspects mentioned above, or to the values set forth above. This can be particularly true of sperm cells, sperm collection systems, bovine sperm cells, equine sperm cells, sperm cells which have been stained and sorted by their DNA content (such as in sexed sperm cells), sorted male or female bovine sperm cells, and even sorted male or female equine sperm cells.

As can be easily understood from the foregoing, the basic concepts of the present invention may be embodied in a variety of ways. It involves both exercise techniques as well as devices to accomplish the appropriate exercise. In this application, the exercise techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may have been relied upon when drafting the claims for this application. This application will seek examination of as broad a base of claims as deemed within the applicant's right and will be designed to yield a patent covering numerous aspects of the invention both independently and as an overall system.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "orientation nozzle" should be understood to encompass disclosure of an "orienting element", the act of "orienting"—whether explicitly discussed or not—and, conversely, were there only disclosure of the act of "orienting", such a disclosure should be understood to encompass disclosure of an "orientation element" and even a "means for orienting". Such changes and alternative terms are to be understood to be explicitly included in the description.

All references in the disclosure or listed in the information disclosure statement filed with the application are hereby incorporated by reference; however, to the extent statements might be considered inconsistent with the patenting of this/these invention(s) such statements are expressly not to be considered as made by the applicant(s).

Finally, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

What is claimed is:

1. A flow cytometer system, comprising:
    a. a sample injection tube having an injection point through which a sample may be introduced;
    b. a sheath fluid container having a bottom end and wherein said sample injection tube is located within said sheath fluid container;
    c. a sheath fluid port connected to said sheath fluid container;
    d. a single torsional orientation nozzle located at least in part below said injection point; and
    e. an analytical system which senses below said single torsional orientation nozzle.

2. A flow cytometer system as described in claim 1 wherein said single torsional orientation nozzle comprises a single torsional interior surface element.

3. A flow cytometer system as described in claim 2 wherein said single torsional interior surface element comprises a tapered single torsional interior surface element and wherein said tapered single torsional interior surface element is of an ellipse-shape or an oval-shape.

4. A flow cytometer system as described in claim 1 and further comprising:
    a. a first axial motion surface in said nozzle;
    b. a second axial motion surface in said nozzle; and
    c. a limited maximal acceleration differentiation transition area between said first axial motion surface in said nozzle and said second axial motion surface in said nozzle wherein said limited maximal acceleration differentiation transition area is coordinated with said sample so as to be affirmatively limited to maintain a functional sample over its length.

5. A flow cytometer system as described in claim 4 wherein said first axial motion surface comprises a first axial acceleration surface and wherein said second axial motion surface comprises a second axial acceleration surface.

6. A flow cytometer system as described in claim 5 wherein said nozzle has acceleration values caused by its internal surface and wherein said acceleration values are selected from a group comprising:

not more than about 0.16 m/sec per micron, not more than about 0.05 m/sec per micron away from the vicinity of the exit orifice, not more than about 0.10 m/sec per micron away from the vicinity of the exit orifice, not more than about 0.13 m/sec per micron away from the vicinity of the exit orifice, not more than about 0.16 m/sec per micron in the vicinity of the exit orifice, not more than about 0.20 m/sec per micron in the vicinity of the exit orifice, not more than about 0.23 m/sec per micron in the vicinity of the exit orifice, not more than about $100 \times 10^{-3}$ m/sec per micron at a distance of more than 300 um away from the exit orifice, not more than about $50 \times 10^{-3}$ m/sec per micron at a distance of more than 300 um away from the exit orifice, not more than about $25 \times 10^{-3}$ m/sec per micron at a distance of more than 300 um away from the exit orifice, such acceleration values with respect to axial location as do not discontinuously change along a central axis, not more than about $100,000 \times 10^{-6}$ m/sec per micron$^2$, not more than about $100,000 \times 10^{-6}$ m/sec per micron$^2$, not more than about $2,000 \times 10^{-6}$ m/sec per micron$^2$, not more than about $1,100 \times 10^{-6}$ m/sec per micron$^2$, not more than about $100,000 \times 10^{-6}$ m/sec per micron$^2$ away from the vicinity of the exit orifice, not more than about $50,000\times10^{-6}$ m/sec per micron$^2$ away from the vicinity of the exit orifice, not more than about $10,000\times10^{-6}$ m/sec per micron$^2$ away from the vicinity of the exit orifice, not more than about $5,000\times10^{-6}$ m/sec per micron$^2$ away from the vicinity of the exit orifice, not more than about $1,000\times10^{-6}$ m/sec per micron$^2$ away from the vicinity of the exit orifice, not more than about $300\times10^{-6}$ m/sec per micron$^2$ away from the vicinity of the exit orifice, not more than about $200\times10^{-6}$ m/sec per micron$^2$ at a distance of more than 300 um away from the exit orifice, not more than about $100\times10^{-6}$ m/sec per micron$^2$ at a distance of more than 300 um away from the exit orifice, such rate of change of acceleration values with respect to axial location as do not discontinuously change along a central axis, and such rate of change of acceleration values with respect to axial location as do not change sign along a central axis away from the vicinity of the exit orifice.

7. A flow cytometer system as described in claim 4 wherein said limited maximal acceleration differentiation transition area comprises a unitary surface.

8. A flow cytometer system as described in claim 4 wherein said limited maximal acceleration differentiation transition area comprises a unitary exit orifice.

9. A flow cytometer system as described in claim 4 wherein said analytical system which senses below said nozzle operates at a rate selected from a group comprising at least 500 sorts per second, at least 1000 sorts per second, and at least 1500 sorts per second.

10. A flow cytometer system as described in claim 4 and further comprising a pressurization system to which said flow cytometer system is responsive and which operates at least about 50 psi.

11. A flow cytometer system as described in claim 9 and further comprising a sperm collection system.

12. A flow cytometer system as described in claim 10 and further comprising a sperm collection system.

13. A flow cytometer system as described in claim 4, 7, 8, 9, or 10 wherein said sample comprises sperm cells selected from a group comprising bovine sperm cells and equine sperm cells.

14. A sexed sperm specimen produced with a flow cytometer system as described in claim 11 or 12.

15. A flow cytometer system as described in claim 14 wherein said sample comprises sperm cells selected from a group comprising bovine sperm cells and equine sperm cells.

16. A mammal produced through use of a sexed sperm specimen produced with a flow cytometer system as described in claim 11 or 12.

17. A flow cytometer system as described in claim 16 wherein said sample comprises sperm cells selected from a group comprising bovine sperm cells and equine sperm cells.

18. A flow cytometer system as described in claim 3 wherein said tapered, elliptical-like, single torsional interior surface element comprises:

a. an ellipse-like demarcation location located at about said injection point; and b. an ellipticity-decreasing zone extending from below said ellipse-like demarcation location.

19. A flow cytometer system as described in claim 3 wherein said tapered, elliptical-like, single torsional interior surface element comprises:

a. an ellipticity-increasing zone;

b. an ellipse-like demarcation location downstream from said ellipticity-increasing zone; and c. an ellipticity-decreasing zone extending from said ellipse-like demarcation location.

20. A flow cytometer system as described in claim 18 and further comprising:

a. a conical zone located below said ellipticity-decreasing zone;

b. a cylindrical zone located below said conical zone; wherein both said conical zone and said cylindrical zone comprises a laminar flow surface;

c. a circular exit orifice located below said cylindrical zone;

d. an oscillator to which said circular exit orifice is responsive; and e. a flow cytometry sorting system below said single torsional orientation nozzle.

21. A flow cytometer system as described in claim 19 and further comprising:

a. a conical zone located below said ellipticity-decreasing zone;

b. a cylindrical zone located below said conical zone; wherein both said conical zone and said cylindrical zone comprises a laminar flow surface; and c. a circular exit orifice located below said cylindrical zone;

d. an oscillator to which said circular exit orifice is responsive; and e. a flow cytometry sorting system below said single torsional orientation nozzle.

22. A flow cytometer system as described in claims 18 wherein said tapered, elliptical-like, single torsional interior surface element, said conical zone, and said cylindrical zone are unitary.

23. A flow cytometer system as described in claims 20 wherein said tapered, elliptical-like, a single torsional interior surface element, said conical zone, said cylindrical zone, and said circular exit orifice are unitary.

24. A flow cytometer system as described in claim 22 wherein said ellipse-like demarcation location has a major axis and a minor axis having a ratio, and wherein said ratio of said major axis to minor axis comprises a ratio which maintains a functional sample.

25. A flow cytometer system as described in claim 24 wherein said major axis of said desired ellipse-like demarcation location is about 2.2 mm and wherein said minor axis of said desired ellipse-like demarcation location is about 1.0 mm.

26. A flow cytometer system as described in claim 19 wherein said ellipse-like demarcation location has a major axis and a minor axis, wherein said major axis of said desired ellipse-like demarcation location is about 2.2 mm and wherein said minor axis of said desired ellipse-like demarcation location is about 1.0 mm.

27. A flow cytometer system as described in claim 22 wherein said single torsional orientation nozzle has a downstream direction, wherein said ellipticity-decreasing zone has cross sections and cross section areas, wherein said cross sections of said ellipticity-decreasing zone undergo transitional changes from ellipse-like shapes to circular shapes downstream, and wherein said cross section areas become progressively smaller downsteam.

28. A flow cytometer system as described in claim 27 wherein each of said cross sections of said ellipticity-decreasing zone has a major axis and a minor axis and wherein said major axis and said minor axis progressively become equal downstream.

29. A flow cytometer system as described in claim 21 wherein said conical zone is about 0.3 mm in height.

30. A flow cytometer system as described in claim 29 herein said cylindrical zone is about 0.15 mm in height.

31. A flow cytometer system as described in claim 2 wherein said single torsional interior surface element comprises a gradually tapered, single torsional interior surface element.

32. A flow cytometer system as described in claim 31 wherein said gradually tapered, single torsional interior surface element comprises an interior surface element that tapers at about 23°.

33. A flow cytometer system as described in claim 19 wherein said tapered, single torsional interior surface element comprises an interior surface element that tapers at about 23°.

34. A flow cytometer system as described in claim 23 wherein said single torsional orientation nozzle comprises a single torsional, ceramic orientation nozzle.

35. A flow cytometer system as described in claim 22 wherein said single torsional orientation nozzle has a height and a top with an outer diameter, and wherein said height is about 13 mm, and wherein said outer diameter about 6 mm.

36. A flow cytometer system as described in claim 20 wherein said flow cytometer system comprises a circular exit orifice, and wherein said tapered, elliptical-like, single torsional interior surface element has a mouth and wherein said mouth is about 5.25 mm in diameter and said circular exit orifice is about 0.07 mm in diameter.

37. A flow cytometer system as described in claim 35 wherein said flow cytometer system comprises a circular exit orifice, and wherein said tapered, elliptical-like, single torsional interior surface element has a mouth and wherein said mouth is about 5.25 mm in diameter and said circular exit orifice is about 0.07 mm in diameter.

38. A flow cytometer system as described in claim 36 wherein said conical zone has a top with an inner diameter, and wherein said inner diameter at said top of said conical zone is about 0.19 mm.

39. A flow cytometer system as described in claim 37 wherein said conical zone has a top with an inner diameter, and wherein said inner diameter at said top of said conical zone is about 0.19 mm.

40. A flow cytometer system as described in claim 18 wherein said sample injection tube comprises a sample orientation tube.

41. A flow cytometer system as described in claim 40 wherein said orientation-improving sample injection tube comprises a beveled tip.

42. A flow cytometer system as described in claim 41 wherein said beveled tip has a circular mouth and wherein said circular mouth has a diameter of about 0.01 mm.

43. A flow cytometer system as described in claim 41 wherein said tapered, elliptical-like interior zone has a major axis and a minor axis at said injection point, and wherein said major axis of said beveled tip is aligned with said major axis of said tapered, elliptical-like interior zone at said injection point.

44. A flow cytometer system as described in claim 43 wherein said single torsional orientation nozzle has a bottom, wherein said beveled tip has a circular mouth, wherein said flow cytometer system further comprises a circular exit orifice located at said bottom of said single torsional orientation nozzle, and wherein said injection point is located at a distance from said circular exit orifice of said single torsional orientation nozzle at which a sample exiting from said circular mouth of said beveled tip receives minimal torquing forces to achieve an orientationally aligned status.

45. A flow cytometer system as described in claim 44 wherein said injection point is located at a distance from said circular exit orifice at which said orientationally aligned status of said sample is substantially maintained when said sample exits said circular orifice of said single torsional orientation nozzle.

46. A flow cytometer system as described in claim 45 wherein said injection point is located about 6 mm from said circular exit orifice of said single torsional orientation nozzle.

47. A flow cytometer system as described in claim 9 wherein said flow cytometer system has dimensions established according to claims 26, 29, 30, 36, 38 or 46.

48. A flow cytometer system as described in claim 1 wherein said sample comprises sperm cells in a sperm compatible buffer.

49. A flow cytometer system as described in claim 48 wherein said analytical system comprises a flow cytometry sorting system.

50. A flow cytometer system as described in claim 49 and further comprising a sperm compatible collection system.

51. A flow cytometer system as described in claim 49 wherein said sample comprises sperm cells in a sperm compatible buffer and wherein said sperm cells are selected from a group consisting of equine sperm cells and bovine sperm cells.

52. A flow cytometer system as described in claim 51 wherein said flow cytometer system has dimensions established according to claims 26, 29, 30, 36, 38, or 46.

53. A sexed sperm specimen produced with a flow cytometer system as described in any of claims 1, 20, 23, 24, 26, 29, 30, 32, 39, 41, 44, 45, 51, or 52.

54. A mammal produced through use of a sexed sperm specimen produced with a flow cytometer system as described in any of claims 1, 20, 23, 24, 26, 29, 30, 32, 39, 41, 44, 45, 51, or 52.

55. A flow cytometer system as described in claim 18, 23, 26, 29, 30, 32, 37, 39, 42, 46 and further comprising:
  a. a first axial motion surface in said nozzle;
  b. a second axial motion surface in said nozzle; and
  c. a limited maximal acceleration differentiation transition area between said first axial motion surface in said nozzle and said second axial motion surface in said nozzle wherein said limited maximal acceleration differentiation transition area is coordinated with said sample so as to be affirmatively limited to not exceed the practical capabilities of said sample over its length.

56. A flow cytometer system as described in claim 55 wherein said limited maximal acceleration differentiation transition area comprises a unitary surface.

57. A flow cytometer system as described in claim herein said limited maximal acceleration differentiation transition area comprises a unitary exit orifice.

58. A flow cytometer system as described in claim 55 wherein said analytical system which senses below said nozzle operates at a rate selected from a group comprising at least 500 sorts per second, at least 1000 sorts per second, and at least 1500 sorts per second.

59. A flow cytometer system as described in claim 55 and further comprising a pressurization system which operates at least about 50 psi.

60. A flow cytometer system as described in claim 58 and further comprising a sperm collection system.

61. A flow cytometer system as described in claim 59 and further comprising a sperm collection system.

62. A flow cytometer system as described in claim 55 wherein a said sample comprises sperm cells selected from a group comprising bovine sperm cells and equine sperm cells.

63. A flow cytometer system as described in claim 57 wherein a said sample comprises sperm cells selected from a group comprising bovine sperm cells and equine sperm cells.

64. A flow cytometer system as described in claim 58 wherein a said sample comprises sperm cells selected from a group comprising bovine sperm cells and equine sperm cells.

65. A flow cytometer system as described in claim 59 wherein a said sample comprises sperm cells selected from a group comprising bovine sperm cells and equine sperm cells.

66. A sexed sperm specimen produced with a flow cytometer system as described in claim 60.

67. A sexed sperm specimen produced with a flow cytometer system as described in claim 64.

68. A mammal produced through use of a sexed sperm specimen produced with a flow cytometer system as described in claim 60.

69. A mammal produced through use of a sexed sperm specimen produced with a flow cytometer system as described in claim 64.

* * * * *